(12) United States Patent
Kissel et al.

(10) Patent No.: US 8,663,742 B2
(45) Date of Patent: Mar. 4, 2014

(54) DURABLE POLYMER-AEROGEL BASED SUPERHYDROPHOBIC COATINGS, A COMPOSITE MATERIAL

(75) Inventors: David J. Kissel, Anoka, MN (US); Charles Jeffrey Brinker, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 64 days.

(21) Appl. No.: 13/121,150

(22) PCT Filed: Jun. 30, 2009

(86) PCT No.: PCT/US2009/049205
§ 371 (c)(1),
(2), (4) Date: May 4, 2011

(87) PCT Pub. No.: WO2010/033288
PCT Pub. Date: Mar. 25, 2010

(65) Prior Publication Data
US 2011/0206925 A1    Aug. 25, 2011

Related U.S. Application Data

(60) Provisional application No. 61/077,143, filed on Jun. 30, 2008.

(51) Int. Cl.
*B05D 5/00* (2006.01)
(52) U.S. Cl.
USPC ............... 427/387; 427/421.1; 427/427.4; 427/427.5; 427/427.7; 427/428.01; 427/429; 427/430.1; 427/435; 427/443.2; 427/388.1; 427/389.7; 427/389.9; 427/393.5; 427/393.6; 427/394

(58) Field of Classification Search
None
See application file for complete search history.

(56) References Cited

U.S. PATENT DOCUMENTS

| | | | |
|---|---|---|---|
| 7,732,496 B1 * | 6/2010 | Leventis et al. | 516/99 |
| 2002/0032272 A1 * | 3/2002 | Sievers et al. | 524/501 |

(Continued)

FOREIGN PATENT DOCUMENTS

| | | |
|---|---|---|
| EP | 0068671 | 1/1983 |
| EP | 0122483 | 10/1984 |

(Continued)

OTHER PUBLICATIONS

Author Unknown, Chinese Office Action dated Dec. 19, 2012, Chinese Application No. 200980125284.4, filed Jun. 30, 2009, pp. 1-30 (including English translation).

(Continued)

*Primary Examiner* — Erma Cameron
(74) *Attorney, Agent, or Firm* — MH2 Technology Law Group, LLP

(57) ABSTRACT

Provided are polymer-aerogel composite coatings, devices and articles including polymer-aerogel composite coatings, and methods for preparing the polymer-aerogel composite. The exemplary article can include a surface, wherein the surface includes at least one region and a polymer-aerogel composite coating disposed over the at least one region, wherein the polymer-aerogel composite coating has a water contact angle of at least about 140° and a contact angle hysteresis of less than about 1°. The polymer-aerogel composite coating can include a polymer and an ultra high water content catalyzed polysilicate aerogel, the polysilicate aerogel including a three dimensional network of silica particles having surface functional groups derivatized with a silylating agent and a plurality of pores.

13 Claims, 2 Drawing Sheets

(56) References Cited

U.S. PATENT DOCUMENTS

2006/0281828 A1    12/2006    Nakayama et al.
2008/0311398 A1*    12/2008    Bauer et al. .................. 428/402

FOREIGN PATENT DOCUMENTS

| | | |
|---|---|---|
| EP | 1412415 | 4/2004 |
| EP | 1412415 B1 | 11/2008 |
| WO | 2006114420 | 11/2006 |
| WO | 2006114420 A1 | 11/2006 |
| WO | WO 2007/011988 * | 1/2007 |

OTHER PUBLICATIONS

Mulik et al., "Cross-Linking 3D Assemblies of Nanoparticles into Mechanically Strong Aerogels by Surface-Initiated Free-Radical Polymerization", Chemistry of Materials, vol. 20, No. 15, Jul. 17, 2008, pp. 5035-5046.

Li Wei, "Studies on the Silica Aerogel Nanomaterial Prepared by Sol-gel Method", Chinese Doctoral Dissertation & Mater's Theses Full-text Database (Master) Engineering Science and Technology I, No. 2, Jun. 15, 2003, pp. 8, 14, 15 and 26.

Japanese Office Action dated Jun. 24, 2013, Japanese Application No. 2011-516802, filed Dec. 9, 2010, pp. 1-6 (including English translation).

* cited by examiner

DURABLE POLYMER-AEROGEL BASED SUPERHYDROPHOBIC COATINGS, A COMPOSITE MATERIAL

RELATED APPLICATIONS

This application claims priority from U.S. Provisional Patent Application Ser. No. 61/077,143, filed Jun. 30, 2008, which is hereby incorporated by reference in its entirety.

GOVERNMENT RIGHTS

This invention was made with government support under Contract Nos. DE-AC04-94AL85000 between Sandia Corporation and the U.S. Department of Energy and FA9550-06-C-0033 awarded by the U.S. Air Force Of Scientific Research. The U.S. Government has certain rights in this invention.

DESCRIPTION OF THE INVENTION

1. Field of the Invention

The subject matter of this invention relates to protective coatings and, more particularly, to polymer-aerogel composites.

2. Background of the Invention

Aerogels are unique solids with up to 99% porosity. Such large porosities confer a number of useful properties to aerogels, including high surface area, low refractive index, low dielectric constant, low thermal-loss coefficient, and low sound velocity. However, the potential of aerogels has not generally been realized because conventional supercritical aerogel processing is energy intensive and conventional aerogels lack durability. Furthermore, most superhydrophobic coatings contain fluorine which can be environmentally unfriendly and may not be cost effective to manufacture.

Thus, there is a need to overcome these and other problems of the prior art and to provide durable and inexpensive superhydrophobic polymer-aerogel coating.

SUMMARY OF THE INVENTION

According to various embodiments, there is a method for preparing a polymer-aerogel composite coating. The method can include providing a superhydrophobic coating solution, the superhydrophobic coating solution including a surface derivatized polysilicate aerogel dispersed in a first solvent, the polysilicate aerogel including a three dimensional network of silica particles having surface functional groups derivatized with a silylating agent. The method can also include adding a polymer solution to the superhydrophobic coating solution to form a polymer-aerogel blend solution, wherein the polymer solution can include one or more polymers dispersed in a second solvent and dissolving the polymer in the polymer-aerogel blend solution at a first temperature. The method can further forming a polymer-aerogel composite coating by applying the polymer-aerogel blend solution to a substrate surface while keeping the polymer-aerogel blend solution at the first temperature, such that the polymer wets the aerogel in the polymer-aerogel composite coating.

In accordance with various embodiments, there is an article including a surface, wherein the surface comprises at least one region and a polymer-aerogel composite coating disposed over the at least one region, wherein the polymer-aerogel composite coating can include a polymer and an ultra high water content catalyzed polysilicate aerogel, the polysilicate aerogel including a three dimensional network of silica particles having surface functional groups derivatized with a silylating agent and a plurality of pores, wherein the polymer-aerogel composite coating has a water contact angle of at least about 140° and a contact angle hysteresis of less than about 1°.

Additional advantages of the embodiments will be set forth in part in the description which follows, and in part will be obvious from the description, or may be learned by practice of the invention. The advantages will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

DESCRIPTION OF THE EMBODIMENTS

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

As used herein, the terms "hydrophobic" and "hydrophobicity" refer to the wettability of a surface (e.g., a coating surface) that has a water contact angle of approximately 85° or more. The terms "superhydrophobic" and "superhydrophobicity" refer to the wettability of a surface (e.g., a coating surface) that has a water contact angle of approximately 150° or more and very low contact angle hysteresis ($\Delta\theta=\theta_A-\theta_B<1$). Typically, on a hydrophobic surface, for example, a 2-mm-diameter water drop beads up but does not run off the surface when the surface is tilted moderately. As the surface is tilted, the wetting angle at the downhill side of the droplet increases, while the wetting angle at the uphill side of the droplet decreases. Since it is difficult for the advancing (downhill) interface to push forward onto the next increment of solid surface and it is difficult for the receding (uphill) interface to let go of its bit of solid surface, the droplet tends to remain stationary or pinned in place. A hydrophobic surface is described as having a low contact angle hysteresis if the difference between advancing and receding contact angles is less than 1°.

Figure 1:
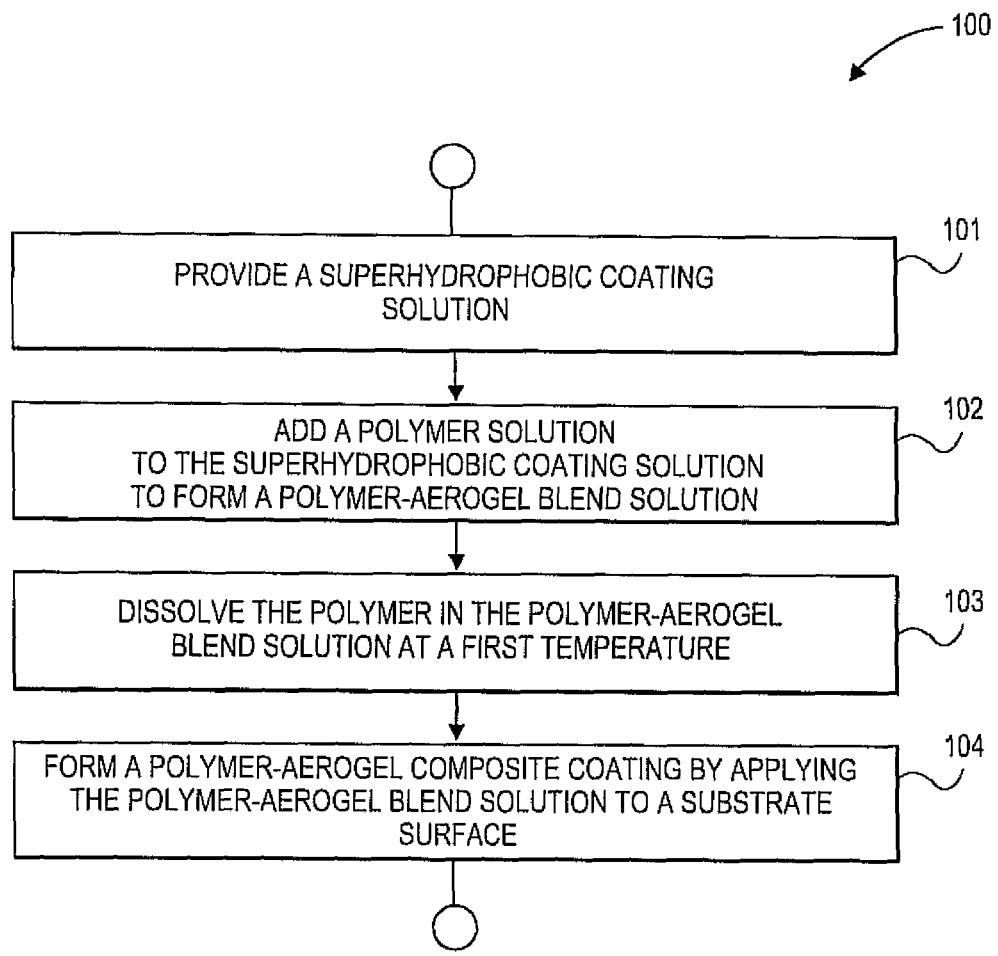
FIG. 1 shows a method for preparing a polymer-aerogel composite coating in accordance with the present teachings.
Figure 2:
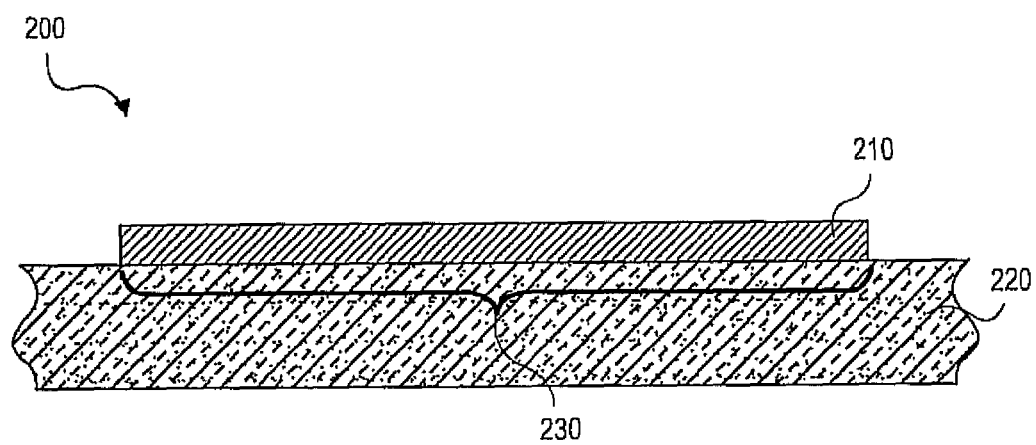
FIG. 2 schematically illustrates a cross section of a portion of an exemplary article in accordance with the present teachings.

In accordance with various embodiments of the present teachings, FIG. 1 shows an exemplary method 100 for preparing a polymer-aerogel composite coating, for example, an exemplary polymer-aerogel composite coating 210 is shown in FIG. 2. The method 100 can include a step 101 of providing a superhydrophobic coating solution. The superhydrophobic coating solution can include a surface derivatized polysilicate aerogel dispersed in a first solvent, the polysilicate aerogel including a three dimensional network of silica particles having surface functional groups derivatized with a silylating agent.

In various embodiments, the step 101 of providing a superhydrophobic coating solution can include providing an ultra high water content acid catalyzed polysilicate aerogel formed using a third solvent, at least one alkoxy silane precursor, water, and an acid, wherein the polysilicate aerogel can include a three dimensional network of silica particles having surface functional groups and a plurality of pores. In various embodiments, a fluid can be disposed in the plurality of pores. Exemplary fluid can include, but is not limited to, first solvent, one or more reaction products of the acid catalyzed hydrolysis of the alkoxy silane, and un-reacted materials such as, for example, alkoxy silane precursor.

In various embodiments, the alkoxy silane precursor can be organically modified silane monomers having a general formula of, for example, $(R')_x Si(OR)_{4-x}$, wherein x is 1 or 2 and R and R' can be the same or different and can include an organic group, such as, for example, an alkyl, an alkenyl, an alkynyl, an aryl group, or combinations thereof. The alkoxy silane precursor can include one or more silane compounds including, but not limited to, methyltrimethoxy silane, vinyltrimethoxy silane, dimethyldiethoxy silane, methacryloxypropyltrimethoxy silane, mercaptopropyltrimethoxy silane, chloropropyltrimethoxy silane, bromopropyltrimethoxy silane, iodopropyltrimethoxy silane, and chloromethyltrimethoxy silane, tetraethoxysilane, tetramethoxysilane, and 1,2-bis(triethoxysilyl)ethane. In some embodiments, the third solvent can be any suitable liquid such as, for example, methanol, ethanol, and any organic solvent at least partially miscible with water. In other embodiments, the acid can be any suitable acid such as, for example, 1.0 N hydrochloric acid and any source of hydrogen ions.

In certain embodiments, the ultra high water content acid catalyzed polysilicate aerogel can be formed using a third solvent, at least one alkoxy silane precursor, water, and an acid, such that a molar ratio of water to alkoxy silane precursor can be in the range of about 10 to about 80, which leads to the distinction of 'ultra high water' content. In some embodiments the molar ratio of water to alkoxy silane precursor can be greater than about 80. In various embodiments, the polysilicate aerogel can be formed by first adding the third solvent to the alkoxy silane precursor, followed by the addition of water and the acid to form a reaction mixture. The reaction mixture can then be agitated and placed at a temperature in the range of about 15° C. to about 80° C. for a period of approximately 1 day to approximately 90 days, and in some cases by placing the reaction mixture at a temperature in the range of about 40° C. to about 60° C. for a period of approximately 3 days to approximately 10 days. Upon the completion of the reaction, the polysilicate aerogel can be rather firm and can have appearance from transparent to opaque depending upon the third solvent used. The polysilicate aerogel should not be loose at this stage; tapping the bottom of the reaction vessel should result in a reverberation throughout the polysilicate aerogel. Excess water and higher levels of acid catalyst can render the hydrolysis portion of the synthesis the dominating process and limiting the condensation. U.S. Patent Application Publication No. 20080113188 and Master's thesis of David J. Kissel entitled, "Mechanical property characterization of sol-gel derived nanomaterials using an acoustic wave technique", May 2007, describe in detail the sol-gel method of forming a silica gel, the disclosures of which are incorporated by reference herein in their entirety.

The step 101 of providing a superhydrophobic coating solution can also include replacing the fluid disposed in the plurality of pores of the polysilicate aerogel with a fourth solvent. In various embodiments, the polysilicate aerogel can be broken up to form a broken gel before adding a second solvent to the broken gel. Any suitable solvent immiscible with the third solvent can be used as the fourth solvent, such as, for example, hexane. The broken gel in the fourth solvent can be kept at a temperature in the range of about 40° C. to about 60° C. for at least about 30 minutes to allow solvent exchange. And finally excess of the fourth solvent and the fluid can be removed from the broken gel. These steps can be repeated at least once, preferably thrice to allow replacement of most of the fluid disposed in the plurality of pores of the polysilicate aerogel. Fresh fourth solvent can be added to the polysilicate aerogel before storing in a cold storage at a temperature of less than about 10° C. However, the polysilicate aerogel can also be stored in fresh fourth solvent at room temperature, because in some cases, the polysilicate aerogel can have a long shelf life at room temperature.

The step 101 of providing a superhydrophobic coating solution can further include derivatizing the surface functional groups of the polysilicate aerogel using one or more silylating agents to form a surface derivatized polysilicate aerogel. In various embodiments, the derivatization of the surface functional groups of the polysilicate aerogel can include gradually adding a silylating agent adding to the polysilicate aerogel due to silylation reaction being exothermic in nature. Any suitable silane can be used as the silylating agent, such as, for example, trimethylchlorosilane, trichloromethylsilane, trichlorooctylsilane, hexamethyldisilazane, and any reactive silane including at least one hydrophobic ligand. Silylation reaction may result in bubbling of the solvent and once the bubbling stops, the polysilicate aerogel can be stored in the silylating agent at a temperature in the range of about 40° C. to about 60° C. for about 6 hours to about 10 hours to form a surface derivatized polysilicate aerogel and an excess of the silylating agent can be removed. While not intending to be bound by any specific theory, it is believed that the second solvent helps in the transport of the silylating agent for reaction with the surface functional groups, such as, for example, surface hydroxyl moieties of the polysilicate aerogel.

The step 101 of providing a superhydrophobic coating solution can also include forming a coating solution of the surface derivatized polysilicate aerogel in the first solvent. In various embodiments, the coating solution of the surface derivatized polysilicate aerogelgel in the first solvent can be formed by first washing the surface derivatized polysilicate aerogel with an excess of fourth solvent and washing the surface derivatized polysilicate aerogelgel with the first solvent at least twice before adding the first solvent to the surface derivatized polysilicate aerogel to form a coating solution. In certain embodiments, the surface derivatized polysilicate aerogel can be sonicated to break up aggregates and redispersed the surface derivatized polysilicate aerogel in the first solvent. Any suitable first solvent can be used, such as, for example, ethanol. In some embodiments, the first solvent can be the same as the third solvent. In other the first solvent can be different from the third solvent. In various embodiments, the surface derivatized polysilicate aerogel in the superhydrophobic coating solution can have a concentration in the range of about 0.1 wt. % to about 30 wt. % and in other cases from about 0.5 wt. % to about 10 wt. %. In some embodiments, the first solvent can be the same as the third solvent.

Referring back to FIG. 1, the method 100 for preparing a polymer-aerogel composite coating can also include a step 102 of adding a polymer solution to the superhydrophobic coating solution to form a polymer-aerogel blend solution, wherein the polymer solution can include one or more polymers dispersed in a second solvent. Any suitable polymer can be used in the formation of the polymer-aerogel blend solution that can bond with the aerogel matrix and provide structural reinforcement. Exemplary polymer can be any suitable copolymer, homopolymer, or polymer blend of one or more polymers, including, but not limited to, poly(methyl methacrylate), polystyrene, poly(butyl methacrylate), poly(tert-butyl methacrylate), poly(methyl acrylate), poly(butyl acrylate), poly(tert-butyl acrylate), poly(perfluorooctyl methacrylate), and any suitable vinyl polymer. Any suitable second solvent can be used to dissolve the polymer, such as, for example, toluene, acetone, xylene, and ethyl acetate. In some cases the second solvent can be a system of solvents rather than a single solvent. The polymer in the polymer solution can have any suitable concentration depending upon various factors, including, but not limited to, polymer type, molecular weight of the polymer, molecular weight distribution of the polymer, etc. In some cases, the polymer in the polymer solution can have a concentration in the range of about 1 wt. % to greater than about 50 wt. % and in other cases from about 5 wt. % to about 50 wt. %. In various embodiments, the superhydrophobic coating can be present in a major amount and the polymer solution can be present in a minor amount, wherein the major amount refers to volume fraction of more than about 0.5 by and minor amount refers to volume fraction of less than about 0.5. In some cases, the polymer solution can be added to the superhydrophobic coating solution at a volume fraction of about 0.05 to about 0.25 and in other cases about 0.1 to about 0.15. However, the polymer solution can be added to the superhydrophobic coating solution in any desired amount.

The method 100 for preparing a polymer-aerogel composite coating can also include a step 103 of dissolving the polymer in the polymer-aerogel blend solution at a first temperature and a step 104 of forming a polymer-aerogel composite coating by applying the polymer-aerogel blend solution to a substrate surface while keeping the polymer-aerogel blend solution at the first temperature or at a temperature greater than the first temperature, such that the polymer wets the aerogel in the polymer-aerogel composite coating. In some embodiments, the step of dissolving the polymer in the polymer-aerogel blend solution at a first temperature can include heating the polymer-aerogel blend solution along with stirring at a first temperature until the polymer dissolves. In some embodiments, the first temperature can be at least about 100° C., in other cases at least about 50° C., and in some other cases can be at least about room temperature. In various embodiments, the polymer-aerogel blend solution can be applied to the substrate surface using any suitable technique, such as, for example, dip coating, brush coating, roller coating, spray coating, spin coating, casting, and flow coating. Any suitable material can be used for the substrate surface, such as, for example, metal, silicon wafers, glass, ceramics, plastics, and fabrics. In some embodiments, the step 104 of forming a polymer-aerogel composite coating can further include heating the substrate to a second temperature greater than the first temperature. In certain embodiments, the second temperature can be in the range of about 50° C. to about 300° C. and in some cases about 100° C. to about 250° C. However, in some embodiments, heating the substrate at the second temperature may not be necessary if the polymer component is well dispersed and wets in the aerogel matrix. Furthermore, heating to the second temperature depends on a variety of factors, including, but not limited to, second solvent, polymer, polymer content, etc.

While not intending to be bound by any specific theory, it is believed that during the processing of the polymer-aerogel blend solution, the polymer and the surface derivatized polysilicate aerogel are blended together to produce a phase separation prior to heating. Heating in the range of about 50° C. to about 300° C. causes the polymer to coat/wet the surface derivatized polysilicate aerogel. Furthermore, the fact that the roughness of the surface derivatized polysilicate aerogel is preserved during the deposition allows the retention of the superhydrophobicity of the surface derivatized polysilicate aerogel. Having too much polymer can cause the water contact angle to approach that of the polymer itself.

FIG. 2 schematically illustrates a cross section of a portion of an exemplary article 200, in accordance with various embodiments of the present teachings. The exemplary article 200 can include a surface 220, the surface 220 including at least one region 230 and a polymer-aerogel composite coating 210 disposed over the at least one region 230, wherein the polymer-aerogel composite coating 210 can have a water contact angle of at least about 140° and a contact angle hysteresis of less than about 1°. Any suitable material can be used for the at least one region 230 of the surface 220, including, but not limited to, a metal, a silicon wafer, a glass, a ceramic, a plastic, and a fabric. In various embodiments, the polymer-aerogel composite coating 220 can include one or more polymers and an ultra high water content acid catalyzed polysilicate gel, wherein the polysilicate aerogel can include a three dimensional network of silica particles having surface functional groups derivatized with a silylating agent and a plurality of pores. Any suitable polymer that can bond with the aerogel matrix and provide structural reinforcement can be used in the polymer-aerogel composite coating 210. Exemplary polymer can be any suitable copolymer, homopolymer, or polymer blend of one or more polymers, including, but not limited to, poly(methyl methacrylate), polystyrene, poly(butyl methacrylate), poly(tert-butyl methacrylate), poly(methyl acrylate), poly(butyl acrylate), poly(tert-butyl acrylate), poly (perfluorooctyl methacrylate), or any suitable vinyl polymer. Exemplary silylating agent can include, but are not limited to, trimethylchlorosilane, trichloromethylsilane, trichlorooctylsilane, hexamethyldisilazane, or any reactive silane including at least one hydrophobic ligand. The polymer-aerogel composite coating 210 can include one or more polymers in any suitable amount. In some cases, the polymer can be present in the polymer-aerogel composite coating in an amount from about 5% by volume to about 50% by volume. However, the polymer can be present in the polymer-aerogel composite coating in any suitable amount that can still preserve the functional surface roughness of the aerogel component of the polymer-aerogel composite. In various embodiments, the polymer-aerogel composite coating 210 can have a thickness from about 0.2 μm to about 3 μm. In various embodiments, the exemplary polymer-aerogel composite coating 210 as disclosed herein can have a low refractive index in the range of about 1.0 to about 1.2 at about 600 nm and can be optically transparent.

In certain embodiments, the polymer-aerogel composite coating 210 can resist corrosion for about 1800 hours or longer. In various embodiments, the exemplary article 200 can include, but is not limited to an antenna, a window, an automobile, an aircraft, a building, a textile, a boat, a partially and/or fully submerged structure in water and the polymer-aerogel composite coating 210 can be used for a wide variety of applications, including, but not limited to, self-cleaning surface, anti-reflective coating, anti-icing coating, a defogging coating, an anti-microbial coating, a stain resistant coating, and a drag reduction coating in water environment. In some embodiments, the disclosed polymer-aerogel composite coating 210 can be applied on the wings of aircraft for the prevention of ice buildup.

In general, the polymer-aerogel composite coating 210 as disclosed herein offer all the benefits of other superhydrophobic materials, but provides far more durability, including abrasion resistance than conventional aerogels. Furthermore, the polymer-aerogel composite coatings 210 of the present disclosure are less costly and are safe for biological applications. Also, by not utilizing fluoro-alkyl silanes and similar fluorinated reagents in the manufacture of the polymer-aerogel composite coating 210, of the present disclosure, the polymer-aerogel composite coating 210 and the methods 100 of making them are environmentally friendly.

Examples are set forth herein below and are illustrative of different amounts and types of reactants and reaction conditions that can be utilized in practicing the disclosure. It will be apparent, however, that the disclosure can be practiced with other amounts and types of reactants and reaction conditions than those used in the examples, and the resulting devices various different properties and uses in accordance with the disclosure above and as pointed out hereinafter.

EXAMPLES

Example 1

Preparation of Polymeric Component, poly(methyl methacrylate) for the Polymer-Aerogel Composite The polymer, poly(methyl methacrylate) was prepared in about 25 ml scintillation vial without a cap. Methyl methacrylate was polymerized thermally using azobisisobutyronitrile (AIBN) as an initiator and dodecanethiol as a chain transfer agent to skew the resulting molecular weight distribution. The weight fractions of the reagents used to prepare the polymer are given in Table 1.

TABLE 1

| Material Name | weight fraction |
| --- | --- |
| Methyl methacrylate | 0.982800 |
| Azobisisobutyronitrile (AIBN) | 0.009828 |
| Dodecanethiol | 0.007371 |

After thorough mixing of the regents, the solution was set on a hot plate at a temperature of about 170° C. For UV-curing, roughly the same weight fraction of photoinitiator was used and out gassing followed by nitrogen purging was done. After polymerization, the polymer was dissolved in toluene followed by filtration and precipitation in ethanol for removal of residual monomer. After removing ethanol, the polymer was dissolved again in toluene at about 10 weight %. This solution was then added to the superhydrophobic coating solution to produce the composite material.

Example 2

Formation of Superhydrophobic Coating Solution

TABLE 2

| Material Name | vol. fraction | for 100 mL gel volume |
| --- | --- | --- |
| Methanol | 0.0832 vol/vol | 8.32 mL |
| Tetramethylorthosilicate (TMOS) | 0.0989 vol/vol | 9.89 mL |
| Dionized Water | 0.8155 vol/vol | 81.55 mL |
| 1.0N Hydrochloric Acid (HCl) | 0.0024 vol/vol | 0.24 mL |

Combined the reagents given in Table 2 according to the order in which they are listed. Agitated the reaction mixture and placed at about 50° C. for a period of approximately 120 hours. Upon the completion of the reaction, a gel was formed. The gel had an opaque appearance and was rather firm. Broke up the gel with a clean utensil (e.g. stir rod, spatula, etc.) and added approximately 100 ml of hexane to the broken gel in the reaction vessel. Allowed solvent exchange for at least 30 minutes at about 50° C. After solvent exchange period, removed excess hexane with a glass pipet and/or syringe and repeated the hexane wash at least once more. After draining excess hexane, the gel was placed in a cold storage in fresh hexane. Added approximately 50 ml of trimethylchlorosilane (TMCS) (also referred to as chlorotrimethylsilane) in about 8 ml to about 12 ml increments to the gel gradually due to the reaction's exothermic nature. As soon as the bubbling stopped, the reaction vessel was closed and placed at about 50° C. for at least about 8 hours. Removed the excess TMCS with a glass pipet and washed with excess hexane (approximately 100 ml). Repeated the hexane washing at least once more. After removal of the excess hexane, washed with excess ethanol (approximately 100 ml) as was done with hexane and repeated the ethanol wash at least once prior to the solution preparation. Removed excess ethanol from the last washing step and added ethanol at a volume appropriate for the desired thickness of the superhydrophobic coating.

Example 3

Preparation of Polymer-Aerogel Composite Coating

In an about 25 ml scintillation vial, added the superhydrophobic coating solution of Example 2 at a volume fraction of about 0.8696. Added the polymer/toluene solution of Example 1 at a volume fraction of about 0.1304 to the superhydrophobic coating solution of Example 2 to form a polymer-aerogel blend solution. Heated the polymer-aerogel blend solution to about 50° C. and agitated until the polymer was dissolved. Applied the polymer-aerogel blend solution to a substrate surface while keeping the polymer-aerogel blend solution 50° C. to ensure proper dispersion of the polymer within the aerogel matrix. After coating, the substrate was heated at a temperature in the range of about 180° C. to about 200° C. for at least about 2 minutes to form a polymer-aerogel composite film having a thickness of about 144 nm. The as is polymer-aerogel composite film showed a water contact angle of about 159.40° and 159.30°. After destructive wearing testing, the polymer-aerogel composite film showed a water contact angle of about 143.00° and 142.50°. The destructive wearing testing was done by vigorously rubbing the polymer-aerogel composite film with a finger covered by a rubber glove. Thus, the polymer-aerogel composite film showed abrasion resistance.

While the invention has been illustrated respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." As used herein, the phrase "one or more of", for example, A, B, and C means any of the following: either A, B, or C alone; or combinations of two, such as A and B, B and C, and A and C; or combinations of three A, B and C.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for preparing a polymer-aerogel composite coating comprising:
   providing a superhydrophobic coating solution, the superhydrophobic coating solution comprising a surface derivatized polysilicate aerogel dispersed in a first solvent, the polysilicate aerogel comprising a three dimensional network of silica particles having surface functional groups derivatized with a silylating agent;
   blending a polymer solution and the superhydrophobic coating solution to form a polymer-aerogel solution, wherein the polymer solution comprises one or more polymers dispersed in a second solvent;
   dissolving the polymer in the polymer-aerogel blend solution at a first temperature; and
   forming, a polymer-aerogel composite coating by applying the polymer-aerogel blend solution to a substrate surface while keeping the polymer-aerogel blend solution at the first temperature, such that the polymer wets the aerogel in the polymer-aerogel composite coating,
   wherein the surface derivatized polysilicate aerogel is an ultra high water content acid catalyzed polysilicate aerogel formed using a third solvent, at least one alkoxy silane precursor, water, and an acid, such that a molar ratio of water to alkoxy silane precursor is in the range of about 10 or more, wherein the polysilicate aerogel comprises a three dimensional network of silica particles having surface functional groups and a plurality of pores, and wherein a fluid is disposed in the plurality of pores, the fluid comprising the third solvent; and
   prior to blending the polymer solution and the superhydrophobic coating solution, replacing the fluid disposed in the plurality of pores of the polysilicate aerogel with a fourth solvent, wherein the fourth solvent is immiscible with the third solvent.

2. The method for preparing a polymer-aerogel composite coating, according to claim 1, further comprising:
   derivatizing the surface functional groups using a silylating agent to form a surface derivatized polysilicate aerogel; and
   forming a superhydrophobic coating solution of the surface derivatized polysilicate aerogel in the first solvent.

3. The method for preparing a polymer-aerogel composite coating, according to claim 2, wherein the alkoxy silane precursor comprises one or more silane compounds selected from the group consisting of methyltrimethoxy silane, vinyltrimethoxy silane, dimethyldiethoxy silane, methacryloxypropyltrimethoxy silane, mercaptopropyltrimethoxy silane, chloropropyltrimethoxy silane, bromopropyltrimethoxy silane, iodopropyltrimethoxy silane, and chloromethyltrimethoxy silane, tetraethoxysilane, tetramethoxysilane, and 1,2-bis(triethoxysilyl)ethane.

4. The method for preparing a polymer-aerogel composite coating, according to claim 2, wherein the silylating agent comprises at least one compound selected from the group consisting of trimethylchlorosilane, trichloromethylsilane, trichlorooctylsilane, hexamethyldisilazane and a silane comprising at least one hydrophobic ligand.

5. The method for preparing a polymer-aerogel composite coating, according to claim 2, wherein the third solvent is the same as the first solvent.

6. The method for preparing a polymer-aerogel composite coating, according to claim 2, wherein the step of replacing the third solvent present in the plurality of pores of the polysilicate aerogel with the fourth solvent comprises:
   (a) breaking up the ultra high water content acid catalyzed polysilicate aerogel to form a broken gel;
   (b) adding the fourth solvent to the broken gel at a temperature in the range of about 40° C. to about 60° C. for at least about 30 minutes;
   (c) removing a portion of the fourth solvent and the third solvent from the broken gel; and
   (d) repeating steps b and c at least three times.

7. The method for preparing a polymer-aerogel composite coating, according to claim 2, wherein the step of derivatizing the surface functional groups using a silylating agent to form a surface derivatized polysilicate aerogel comprises:
   gradually adding to the polysilicate aerogel a silylating agent, the silylating agent comprising at least one compound selected from the group consisting of trimethylchlorosilane, trichloromethylsilane, trichlorooctylsilane, hexamethyldisilazane and a silane comprising at least one hydrophobic ligand;
   storing the polysilicate aerogel in silylating agent at a temperature in the range of about 40° C. to about 60° C. for about 6 hours to about 10 hours to form a surface derivatized polysilicate aerogel; and
   removing a portion of the silylating agent.

8. The method for preparing a polymer-aerogel composite coating, according to claim 2, wherein the step of forming a coating solution of the surface derivatized polysilicate aerogel in a first solvent comprises:
   washing the surface derivatized polysilicate aerogel with the fourth solvent;
   washing the surface derivatized polysilicate aerogel with the first solvent at least twice; and
   adding the first solvent to the surface derivatized polysilicate aerogel to form a coating solution.

9. The method for preparing a polymer-aerogel composite coating, according to claim 1, wherein the first solvent is the same as the second solvent.

10. The method for preparing a polymer-aerogel composite coating, according to claim 1, wherein the polymer comprises at least one compound selected from the group consisting of poly(methyl methacrylate), polystyrene, poly(butyl methacrylate), poly(tert-butyl methacrylate), poly(methyl acrylate), poly(butyl acrylate), poly(tert-butyl acrylate), poly(perfluorooctyl methacrylate) and a vinyl polymer.

11. The method for preparing a polymer-aerogel composite coating, according to claim 1, wherein the step of forming a polymer-aerogel composite coating comprises applying the polymer-aerogel blend solution using at least one of dip coating, brush coating, roller coating, spray coating, spin coating, casting, and flow coating.

12. The method for preparing a polymer-aerogel composite coating, according to claim 1, wherein the step of forming a polymer-aerogel composite coating further comprises heating the substrate to a second temperature greater than the first temperature.

13. The method for preparing a polymer-aerogel composite coating, according to claim 1, wherein the substrate surface comprises at least one material selected from the group consisting of a metal, silicon, a glass, a ceramic, a plastic and a fabric.

* * * * *